(12) United States Patent
Sotereanos

(10) Patent No.: US 6,616,697 B2
(45) Date of Patent: Sep. 9, 2003

(54) HIP IMPLANT ASSEMBLY

(76) Inventor: Nicholas G. Sotereanos, 2335 Buena Vista Dr., McKeesport, PA (US) 15135

( * ) Notice: Subject to any disclaimer, the term of this patent is extended or adjusted under 35 U.S.C. 154(b) by 0 days.

(21) Appl. No.: 09/805,323

(22) Filed: Mar. 13, 2001

(65) Prior Publication Data

US 2002/0133234 A1 Sep. 19, 2002

(51) Int. Cl.$^7$ .................................................. A61F 2/36
(52) U.S. Cl. ................................. 623/23.26; 623/22.11
(58) Field of Search ............................ 623/22.11, 22.4, 623/22.42–22.46, 23.15, 23.21, 23.22, 23.26, 23.29, 23.3, 23.36, 23.37, 23.39, 23.4, 23.42, 23.44–23.46

(56) References Cited

U.S. PATENT DOCUMENTS

| | | | |
|---|---|---|---|
| 2,718,228 A | 9/1955 | Van Steenbrugghe | |
| 2,947,308 A | * 8/1960 | Gorman | 606/72 |
| 3,859,669 A | * 1/1975 | Shersher | 623/22.44 |
| 4,080,666 A | * 3/1978 | Fixel | 606/64 |
| 4,129,903 A | 12/1978 | Huggler | |
| 4,530,114 A | 7/1985 | Tepic | |
| 4,532,660 A | 8/1985 | Field | |
| 4,621,637 A | 11/1986 | Fishbein | |
| 4,711,233 A | 12/1987 | Brown | |
| 4,715,860 A | 12/1987 | Amstutz et al. | |
| 4,795,473 A | 1/1989 | Grimes | |
| 4,811,632 A | 3/1989 | Salyer | |
| 4,834,756 A | 5/1989 | Kenna | |
| 4,895,573 A | * 1/1990 | Koeneman et al. | 606/89 |
| 4,998,937 A | 3/1991 | Grimes | |
| 5,007,935 A | 4/1991 | Vincent et al. | |
| 5,087,260 A | 2/1992 | Fixel | |
| 5,100,267 A | 3/1992 | Salyer | |

(List continued on next page.)

FOREIGN PATENT DOCUMENTS

| | | |
|---|---|---|
| DE | 30 17 953 | 12/1981 |
| DE | G 91 03 574.0 | 4/1992 |
| DE | 299 21 577 U1 | 2/2000 |
| DE | 200 07 950 U1 | 7/2000 |
| EP | 0 457 222 A1 | 11/1991 |
| EP | 0 567 349 A1 | 10/1993 |
| FR | 1047640 | 12/1953 |
| FR | 1122634 | 9/1956 |
| FR | 80495 | 3/1963 |
| FR | 2689390 | 10/1993 |
| FR | 2697996 | 5/1994 |
| WO | WO 86/03962 | 7/1986 |
| WO | WO 93/16663 | 9/1993 |
| WO | WO 97/25939 | 7/1997 |

OTHER PUBLICATIONS

ESKA–Implants Femoral Neck Prosthesis (FNP), ESKA Implants GmbH & Co., ESKA Advertisement.

Primary Examiner—Kevin Shaver
Assistant Examiner—Michael B. Priddy
(74) Attorney, Agent, or Firm—Kirkpatrick & Lockhart LLP

(57) ABSTRACT

An implant and method for replacement of the proximal portion of a femur, and specifically for replacement of the natural femoral head is provided. The implant includes a body member for insertion, in use, through the natural femoral neck and in substantial alignment therewith; a head member with a spherical portion for engagement with a natural or a prosthetic hip socket; a joining portion for joining the head member to the body member; and a rod for insertion, in use, through the transverse passage of the body member. The rod is designed such that it has a cross-sectional configuration that contacts the cortical surfaces in the bone and inhibits micro-motion within the bone. In addition, the transverse passage of the body member is configured to complement the configuration of the rod such that the need for stabilizing screws toward the distal end of the rod is eliminated when the implant is assembled within the patient.

52 Claims, 16 Drawing Sheets

U.S. PATENT DOCUMENTS

| | | |
|---|---|---|
| 5,116,165 A | 5/1992 | Salyer |
| 5,203,653 A | 4/1993 | Kudla |
| 5,336,268 A | 8/1994 | Rispeter |
| 5,342,366 A | 8/1994 | Whiteside et al. |
| 5,370,706 A * | 12/1994 | Bolesky et al. .......... 623/23.44 |
| 5,376,092 A | 12/1994 | Hein et al. |
| 5,389,107 A | 2/1995 | Nassar et al. |
| 5,458,654 A | 10/1995 | Tepic |
| 5,462,548 A | 10/1995 | Pappas et al. |
| 5,571,203 A | 11/1996 | Masini |
| 5,593,451 A | 1/1997 | Averill et al. |
| 5,709,688 A | 1/1998 | Salyer |
| 5,725,595 A | 3/1998 | Gustilo |
| 5,741,262 A | 4/1998 | Albrektsson et al. |
| 5,755,719 A | 5/1998 | Frieze et al. |
| 5,755,810 A | 5/1998 | Cunningham |
| 5,782,928 A | 7/1998 | Ries et al. |
| 5,800,557 A | 9/1998 | Elhami |
| 5,935,172 A * | 8/1999 | Ochoa et al. .................. 606/77 |

* cited by examiner

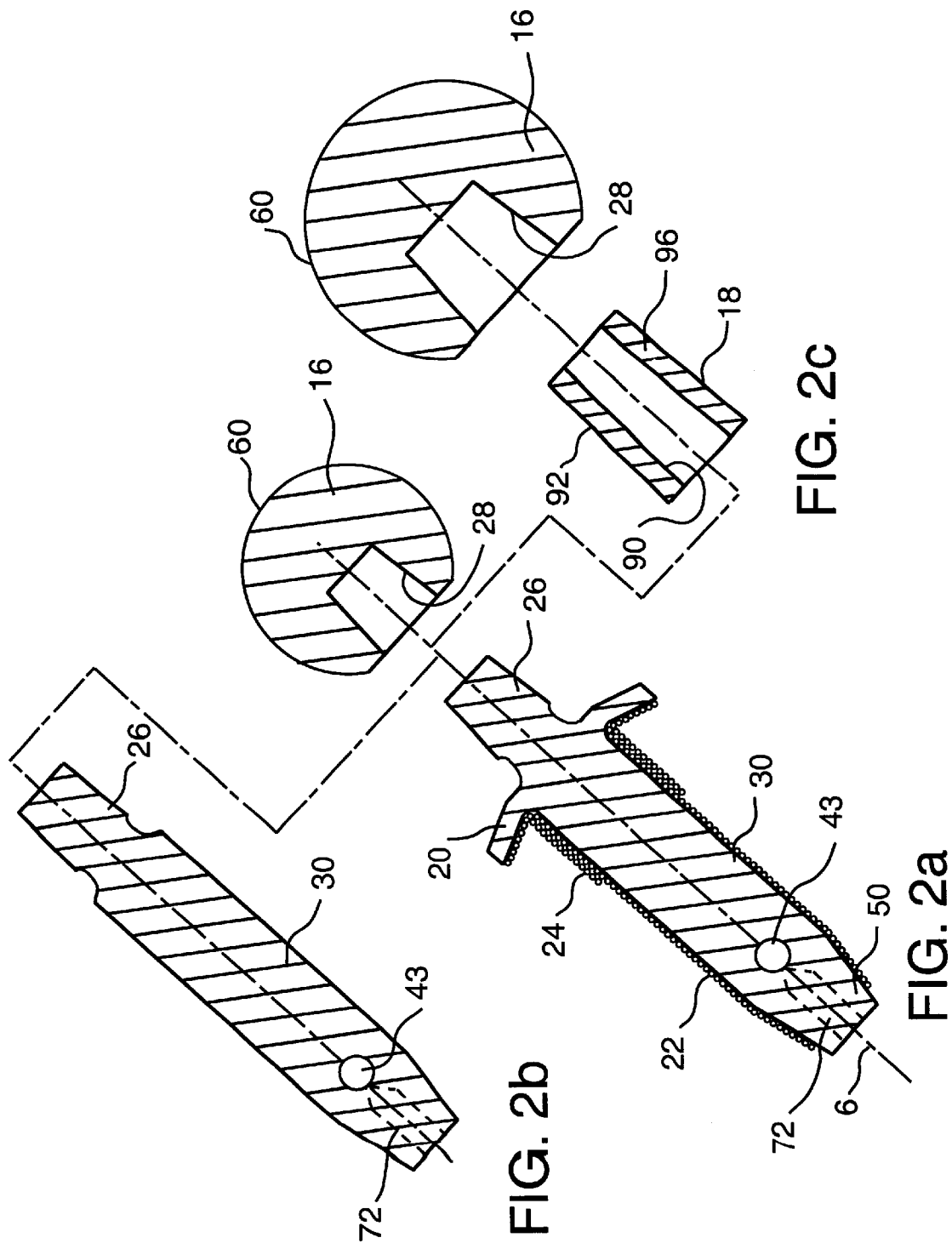

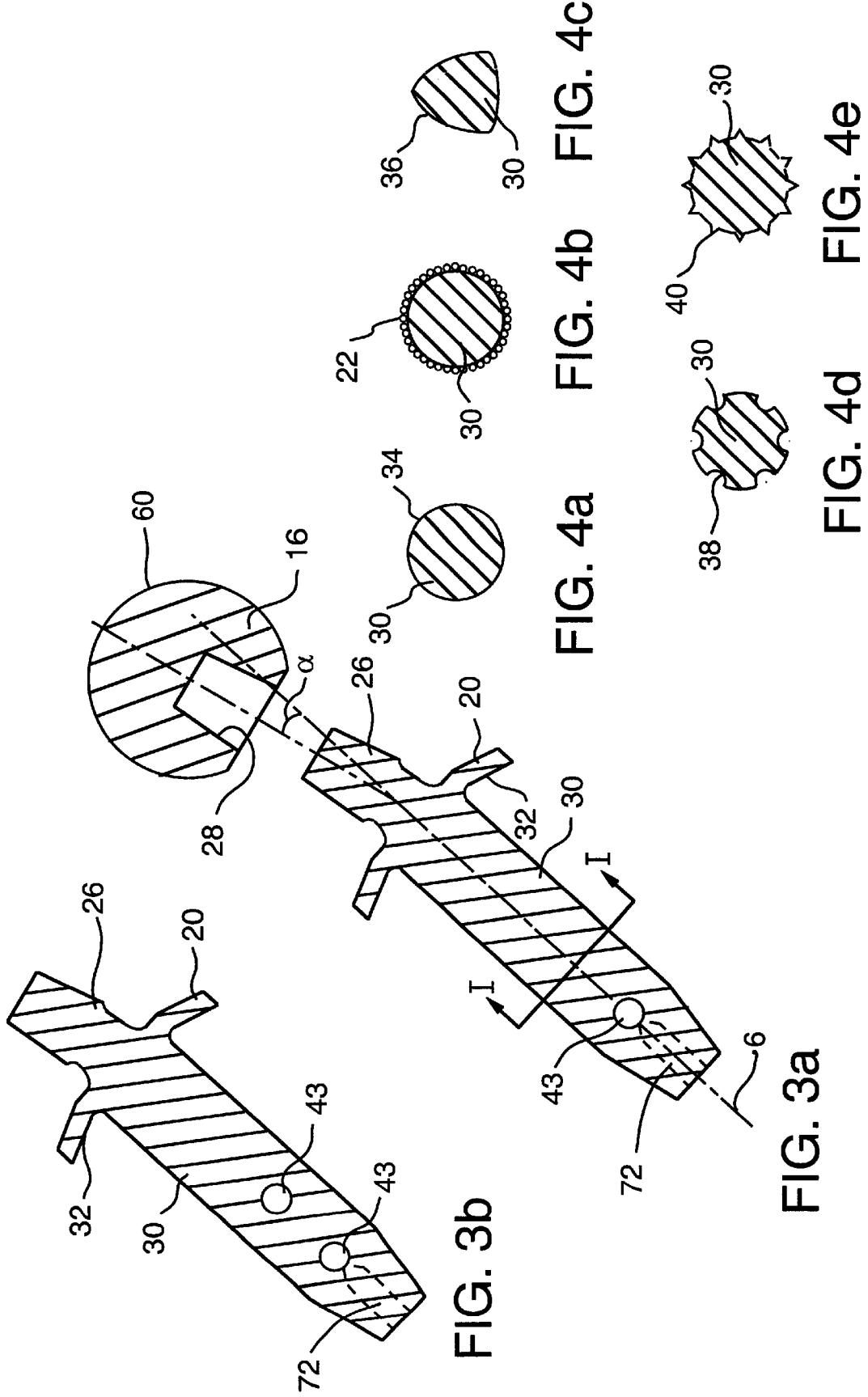

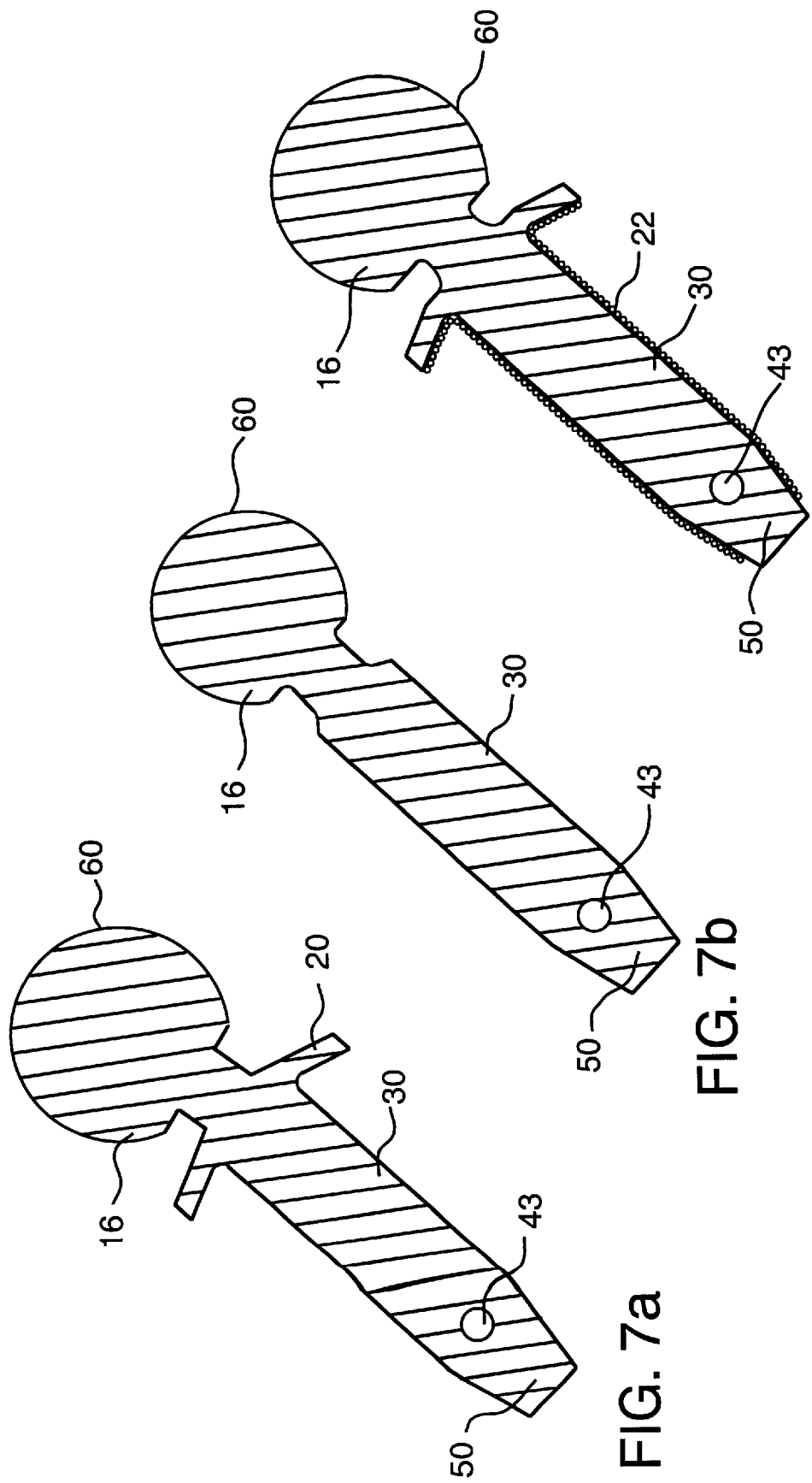

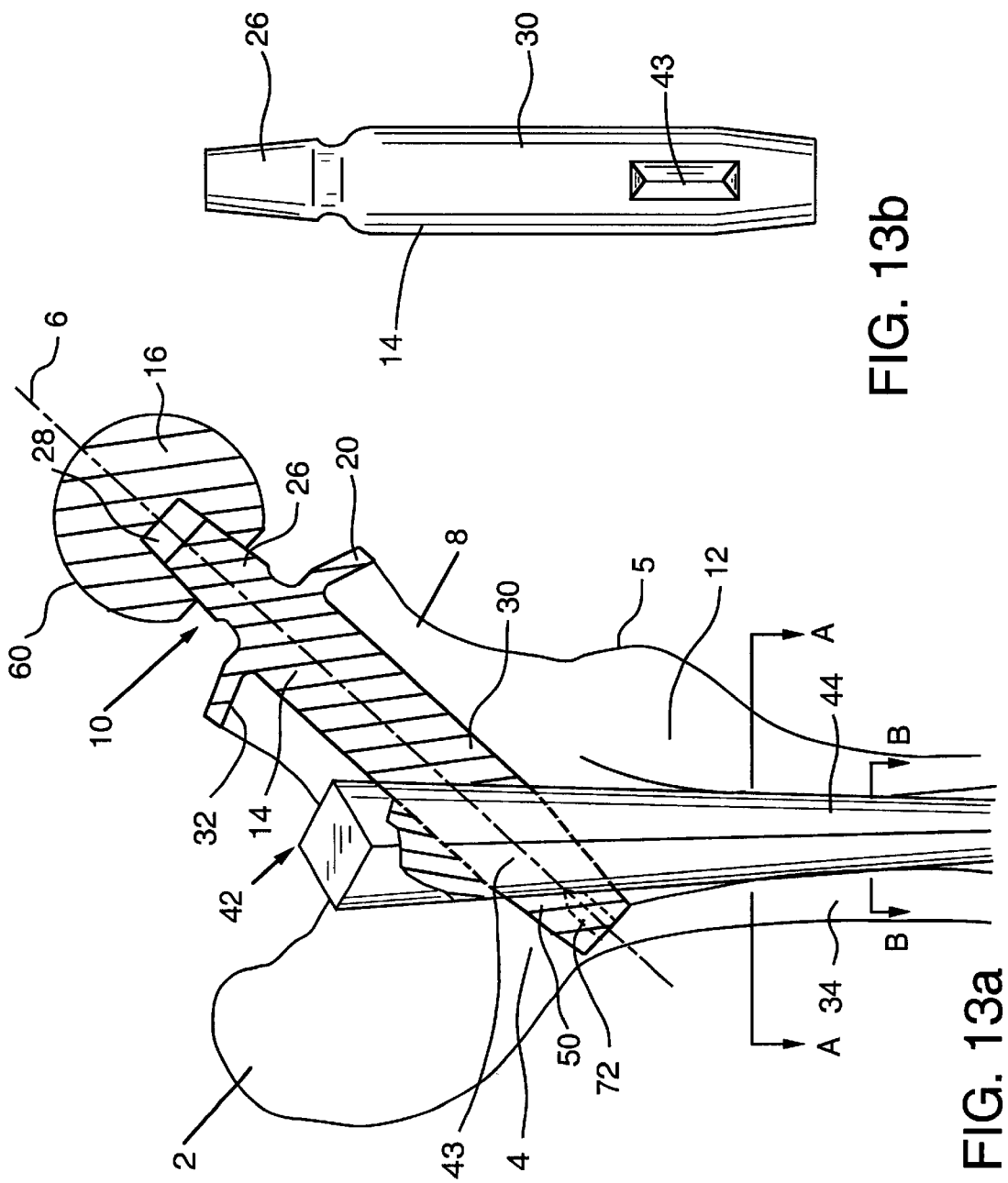

HIP IMPLANT ASSEMBLY

BACKGROUND OF THE INVENTION

1. Field of the Invention

The subject invention relates to femoral implants, and, more particularly, to a modular proximal femoral implant for replacing a femoral head and a method of implanting the same.

2. Description of the Invention Background

Hip replacements are common. A person's hip joint may need to be replaced due to degeneration from severe trauma, such as an automobile accident, or from a plurality of etiologies, such as arthritis or disease. If the degeneration is severe, it may be necessary to replace the natural hip joint with a prosthetic hip. The femoral components of the hip joint are then replaced in whole or in part with a hip prosthesis. While hip implants are generally successful, they usually have to be replaced every few years because of the stress caused by the prosthesis.

A widely used design for replacement of the proximal portion of a femur employs an elongate, often curved, shaft that extends into the medullary canal of the femur. This design has the tendency to place unnatural stresses on the femur which lead to pain and the consequent curtailment of activity for the patient. The useful life of an intramedullary implant is often less than the expected life span of a young patient.

Previously known prostheses for replacing a femoral head that do not extend into the medullary canal have been mechanically complex or have proven troublesome in actual use. Huggler, U.S. Pat. No. 4,129,903 and Grimes, U.S. Pat. No. 4,795,473 are examples of prosthetic implants having a side plate attached to the exterior lateral side of the femur opposite the femoral head. Screws are used to secure the plate to the femur and one or more holes are drilled into the femur for securing the plate to the bone. The additional holes and the stresses at the site of fixation are believed to cause trauma to the bone.

Masini, U.S. Pat. No. 5,571,203 discloses a device having a shaft that extends through a resected portion of the proximal femur, positioned co-axially relative to the longitudinal axis of the femur. The device is secured by a screw or similar locking device that extends into the femur from the lateral side, just below the greater trochanter. It is believed that the natural forces applied to the prosthesis during normal hip motion result in the application of shear forces to the greater trochanter. The shear forces can be harmful to the greater trochanter and can permit micromovement of the prosthesis on the unsecured side.

A conventional method for implanting the above types of femoral head implants is described in *Campbell's Operative Orthopaedics*, (Mosby, 7th ed., 1987) and typically includes making a large incision in the patient's lateral side at the hip joint and through the skin and muscle, dislocating the hip and then sawing off the femoral head. This method is considered invasive because of the need to dislocate the hip and cut through muscle surrounding the hip joint. Invasive procedures increase the trauma to the patient, the potential for complications, recovery time and the cost.

Replacement of the proximal portion of the femur is sometimes necessary due to degenerative bone disorders or trauma to otherwise healthy bone caused by accidental injury. In the latter instance it is desirable to replace the traumatized portion of the bone without causing further trauma to healthy bone. There is a need, therefore, for an implant that replaces a traumatized portion of the femur, but also significantly minimizes stress to the remaining healthy bone and that can be implanted by a method that is not invasive.

SUMMARY OF THE INVENTION

The present invention provides a proximal femoral replacement implant that both reduces trauma to the femur and the time required to perform the implantation. The design of the implant of the present invention transfers forces to the femur in a natural way and minimizes micromotion.

The implant of the present invention includes a body member having a longitudinal axis, a distal end and a proximal end. The body member is configured such that it is positioned in the natural femoral neck with passage of the distal end through the medial side of the femur, or through a reamer hole in the lateral side of the femur. The implant also includes a head member having a distal end and a proximal spherical portion configured for positioning in a natural or prosthetic hip socket, and a joining portion for joining the distal end of the head member to the proximal end of the body member. Furthermore, the implant includes a rod having a longitudinal axis, a distal end and a proximal end. The rod is configured such that it is positioned in the medullary (femoral) canal of the femur with passage through the body member in a direction transverse to the longitudinal axis of the body member.

The implant may also include a collar positioned at the proximal end of the body member and configured for abutting contact, in use, with a proximal surface of the resected femoral neck when the implant is inserted medially.

The body member is preferably configured in cross-section to inhibit rotational motion following implantation. The body member may be triangular, fluted or scalloped in cross-section. Alternatively, the body member may be circular in cross-section.

The body member and the head member may be integrally attached at the joining portion, but may also, and preferably, form modular components for complementary engagement with each other through joining portions. The joining portion preferably includes a first engagement portion and a second engagement portion, the first and second engagement portions being configured for complementary engagement with each other. The joining portion may extend outwardly from the body member at an acute angle relative to the longitudinal axis of the body member to provide anteversion. Alternatively, the joining portion may extend outwardly from the body member in substantial coaxial alignment with the longitudinal axis of the body member. The first engagement portion may be a recess formed either in the body member or the head member for receiving the second engagement portion and the second engagement portion may be a protrusion formed respectively, in the head member or the body member for insertion into the recess.

The modular embodiment of the implant of the present invention also preferably includes an optional member, preferably a sleeve, for altering the position of the spherical portion of the head member relative to the body member. The sleeve has an inner surface and an outer surface and defines a wall therebetween. It is mountable such that, in use, the inner surface slides over the protrusion and the outer surface is received within the recess. The sleeve may be longer in length than the protrusion of the joining portion for extending the distance between the spherical member and the body member. Additional sleeves may be provided wherein the wall has non-uniform, gradual thickness changes such that, in use, the central axis of the sleeve relative to the outer surface of the sleeve is at an acute angle to permit positioning of the head member at an angle relative to the longitudinal axis of the body member when needed.

The present invention further provides a method for implanting the proximal femoral replacement implant of the present invention using a reamer or burr which includes rotating the reamer into engagement with the lateral side of the femur and along the axis of the femoral neck to form a passage therethrough, morselizing the natural femoral head with the reamer or burr while keeping the natural femoral neck substantially intact, inserting the body member of the femoral replacement implant into the passage from the lateral side of the femur, forming another passage from the proximal end of the femur and into the medullary canal of the femur, and inserting a rod of the proximal femoral replacement implant from the proximal end of the femur through the body member and into the medullary canal of the femur.

Other details, objects and advantages of the present invention will become apparent with the following description of the present invention.

BRIEF DESCRIPTION OF THE DRAWINGS

For the purpose of illustrating the preferred embodiments and methods of implantation of the proximal femoral replacement implant of the present invention and not for limiting the same, reference is made to the drawings in which:

FIGS. 2a, b and c represent an exploded cross-sectional view of several components of the modular embodiment of the implant of the present invention;

FIGS. 3a and b are cross-sectional views of two embodiments of the implant of the present invention illustrating an anteverted member for mounting the femoral head member and one or more holes to accept one or more rods;

FIGS. 4a–e illustrate cross-sectional views through line I—I of FIG. 3(a) of the alternative embodiments of the shaft portion of the implant;

FIGS. 7a–c are cross-sectional views of embodiments of the present invention, wherein the body member and the head member form a unitary implant;

FIG. 13a illustrates an alternative embodiment of the rod of the implant. FIG. 13b illustrates an alternative embodiment of the body member of the implant. FIG. 13c is a cross-sectional view across lines A—A and B—B of an alternative embodiment of the rod of the implant.

DETAILED DESCRIPTION OF THE INVENTION

Figure 1:
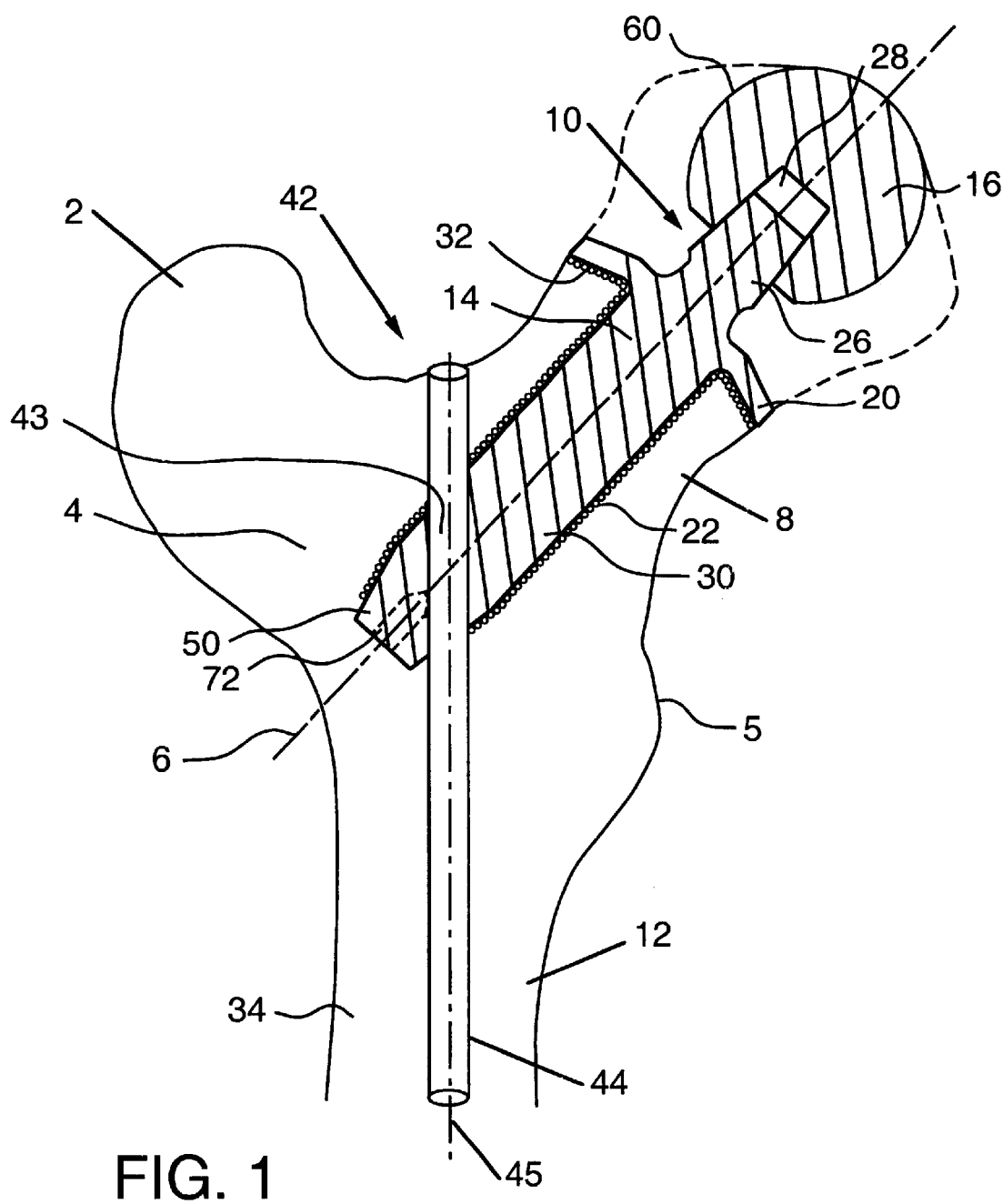
FIG. 1 is a cross-sectional view of an embodiment of the proximal femoral replacement implant of the present invention shown as implanted in a femur.

FIGS. 1 through 12 illustrate various embodiments of the proximal femoral replacement implant 10 of the present invention. Referring to FIG. 1, the modular embodiment of implant 10 is shown as it would appear after implantation in a femur 12. The natural femoral head, illustrated in hidden lines, has been removed, but the femoral neck 8 and the remainder of the femur 12 remain intact.

The modular embodiment of implant 10 includes generally a body member 14, a head member 16, an optional member, such as sleeve 18 (FIGS. 2 and 8) for positioning the head member 16, and a rod 44.

One embodiment of the body member 14 is a solid unitary structure having a symmetrical elongate shaft 30 with a tapered distal end 50, an engagement surface, preferably in the form of a mount or neck 26, and a collar 20.

Referring to FIG. 1, the body member 14 is configured for insertion into the natural femoral neck 8 such that the underside 32 of the collar 20 rests on the resected surface of remaining intact femoral neck 8 and the central longitudinal axis 6 of the shaft 30 is preferably generally in coaxial alignment with the central longitudinal axis of the femoral neck 8. Although some deviation from alignment with the neck axis can be tolerated and would in practice be determined by the surgeon in each case, the axis 6 of shaft 30 preferably extends along the axis of the femoral neck 8 into the extramedullary area 4 in the portion of the femur 12 intermediate the greater and lesser trochanters, 2 and 5 respectively. The shaft 30 does not extend into the medullary canal 34. The body member 14 of the implant 10 is designed to be positioned in the proximal portion of the femur 12. The implant 10 of the present invention thereby avoids two significant causes of stress on the healthy bone of an implant patient.

The collar 20 also aids in properly distributing the forces applied to the femur 12. The force of the patient's weight is distributed by the collar 20 over the resected surface on which the collar 20 rests. The collar 20 may be flat, angled or curved in configuration. The resected surface is preferably cut to match the configuration of the collar 20 so that the collar 20 contacts substantially all of the resected surface of the femur 12. Alternatively, there may be no collar 20. An embodiment of the body member 14 having no collar 20 is shown in FIG. 2b.

The shaft 30 may be made in a variety of cross-sectional configurations. Referring to FIGS. 4a–e, examples include circular 34 (FIG. 4a), circular with beads or another bone ingrowth enhancing surface (FIG. 4b), triangular 36 to complement the cross-sectional shape of the natural femoral neck 8 (FIG. 4c), scalloped 38 (FIG. 4d), and fluted 40 (FIG. 4e). Those skilled in the art will appreciate that a number of cross-sectional configurations may be employed. The triangular 36, scalloped 38 and fluted 40 cross-sectional configurations restrict rotational movement of the shaft 30 after implantation until bone ingrowth progresses enough to secure the implant 10 in position.

The implant 10 also includes a rod 44. Referring to FIG. 1, the rod 44 comprises a longitudinal axis 45, a proximal end and a distal end. The rod 44 is configured for insertion from the proximal end 42 of the femur 12, through the shaft 30 of the body member 14, thus forming a transverse passage 43 through the shaft 30, and into the medullary canal 34 of the femur 12 such that the central longitudinal axis 45 of the rod 44 is preferably generally in coaxial alignment with the central longitudinal axis of the medullary canal 34 of the femur 12. Although some deviation from alignment with the medullary canal 34 can be tolerated and would in practice be determined by the surgeon in each case, the longitudinal axis 6 of the body member 14 and the longitudinal axis 45 of the rod 44 should form approximately a 130° angle.

Figure 10:
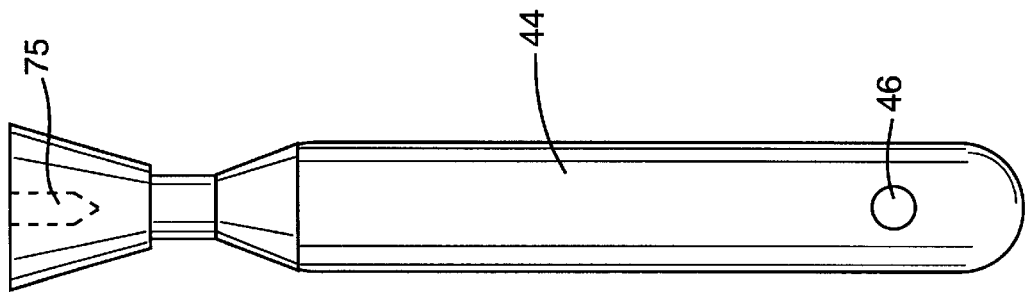
FIG. 10 illustrates an embodiment of the rod of the implant.
Figure 9:
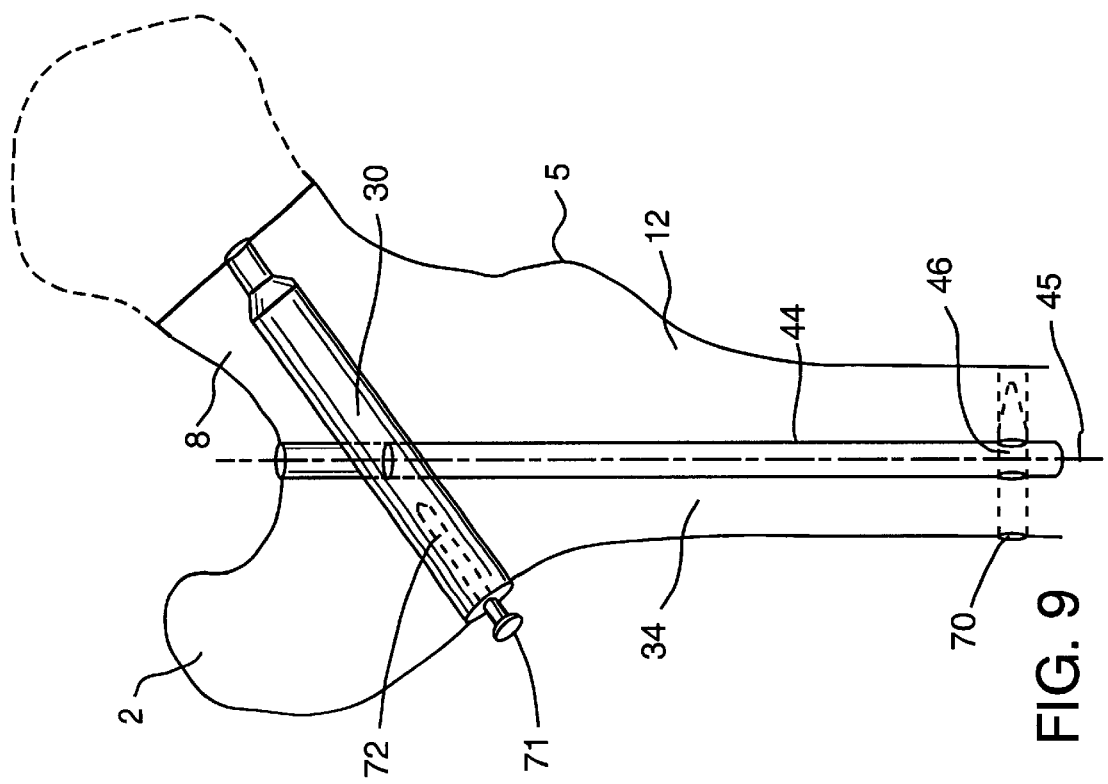
FIG. 9 illustrates an embodiment of the implant as it is inserted in the femur.

The rod 44 can have any cross-sectional configuration. Referring to FIGS. 9&10, the rod 44 may be circular in cross-section, having a cone shaped taper at its proximal end. The cone shaped taper, preferably a $^{12}/_{14}$ taper, enables the body member 14 and the rod 44 to form a taper lock. The taper lock prevents rotation of the rod 44 within the femur 12. Although a taper lock is the preferred means to prevent rotation of the rod 44 within the femur 12, any means to prevent rotation within the femur 12 will suffice. Preferably, the rod 44 has a cross-sectional configuration of a tapered wedge, and as shown in FIG. 13, a dual tapered or elongated diamond shaped wedge. The dual tapered wedge preferably tapers gradually from the proximal end to the distal end of the rod 44 and ends in a flat or pointed tip.

In the embodiment shown in FIG. 1, at least a portion of the surface of shaft 30, the underside 32 of the collar 20, and the rod 44 may have a porous coating 22 to promote bone ingrowth. A most preferred surface coating is made of at least one layer of sintered beads, preferably titanium, cobalt or some other bio-compatible material. Other suitable coating materials may be used, such as hypoxy or hydroxy appetite. A second layer of coating 24, for example, over the portion of shaft 30 adjacent collar 20 provides additional surface area for bone ingrowth. See FIG. 2a. Multiple layers of beads further inhibit rotation and minimize micro-motion of the implant 10 in the femur 12.

Micro-motion is harmful because it wears the inner surface of the bone where it contacts the implant 10, loosening the implant 10 and thereby increasing the potential for the prosthesis to rotate in the femur 12 or lift out of the femur 12. For example, two layers of beads 22 and 24 or other coating material may be positioned on the proximal portion of the shaft 30 where the risk of wear on the femur 12 has been observed to be the greatest. Bone ingrowth can also be enhanced by varying the size of the beads to create different pore sizes. As an alternative to metal beads, the coating may be a plasma sprayed coating or the surface of implant 10 may be roughened by any suitable known grit blasting process.

The body member 14 is preferably from about 50 mm to 120 mm in length and from about 12 mm to 30 mm in diameter. For adult female patients, the natural femoral neck 8 varies in diameter from about 14 mm to 22 mm. For adult male patients, the natural femoral neck 8 varies from about 16 mm to 34 mm in diameter. The length and diameter of the shaft 30 of body member 14 will necessarily be less than the diameter of the proximal femur 12 and the natural femoral neck 8 in which the implant 10 is positioned.

The rod 44 is preferably from about 5.75 inches in length and from about 0.375 inches in diameter. However, the rod 44 can be made in various lengths and diameters to accommodate most, if not all, male and female patients. The length and diameter of the rod 44 will be less than the length and diameter of the shaft of the femur 12 in which the implant 10 is positioned.

The variations in sizes of the implant 10 will fall within the anatomical ranges and constraints of the patient population. In order to accommodate patient differences, the various modular components of the implant 10 of the present invention can be made in a variety of sizes that are interchangeable with other components. In certain circumstances, the implant 10 may be suited for implantation in children.

The body member 14 and the head member 16 are joined by a joining portion, which may be in the form of an engagement surface at the proximal end of the body member 14 adapted for complementary engagement with an engagement surface on the distal end of the head member 16 for securely joining the two components together. A preferred surface that is provided is a protrusion, like that of mount 26, which is preferably tapered for sliding insertion into a complementary recess 28 in the head member 16 for securing the two components together. See FIG. 1. Alternatively, the body member 14 may include a recess 52 for receiving a protrusion, like that of mount 56 on head member 16. See FIG. 5.

The head member 16 includes a generally spherically shaped portion 60 and an engagement surface, such as recess 28 (FIGS. 2 and 3), for complementary engagement with the engagement surface of body member 14, such as mount 26. Alternatively, the engagement surface of the head member 16 may be mount 56 (FIGS. 5 and 6) which is inserted into the engagement surface of the body member 14, recess 52. In those embodiments of head member 16 having a mount 56, an annular portion 62 may be positioned between the spherical portion 60 and mount 56. See FIGS. 5 and 6a. The head member 16 extends from the body member 14 at a distance and angle above the collar 20 suitable to permit the spherical portion 60 to mate with the patient's hip socket (not shown). The degree of extension or angulation will match the anatomy of the particular patient. Like the body member 14, the head member 16 can be made in a variety of sizes to accommodate patient needs. A head member 16 having an enlarged spherical portion 60 is shown in FIG. 2c and in FIG. 6b.

Figure 8:
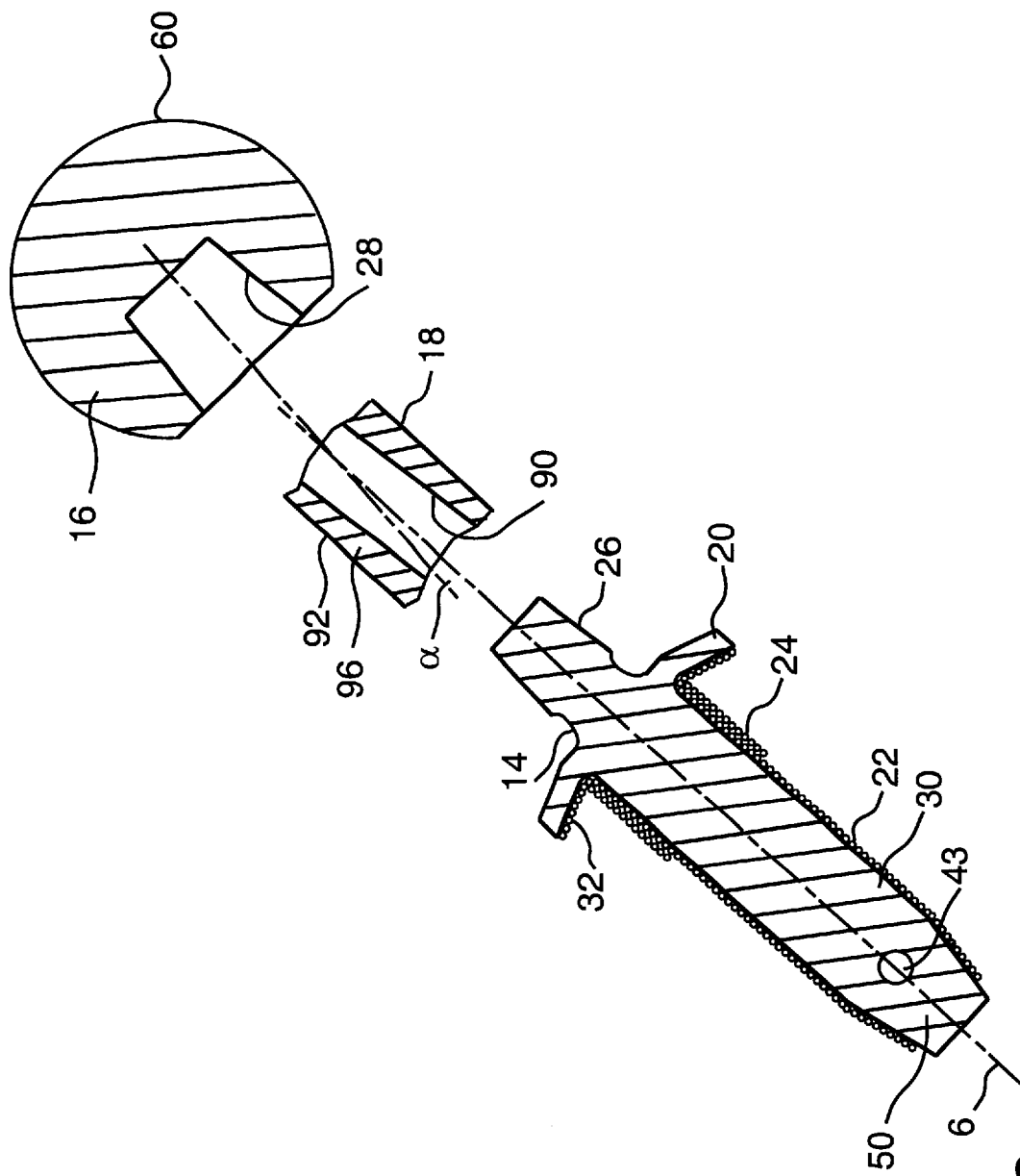
FIG. 8 is a cross-sectional view of an alternative embodiment of the proximal femoral implant of the present invention showing a sleeve member for introducing anteversion.

Referring to FIG. 2c and FIG. 8, an optional member, such as sleeve 18 for positioning the spherical portion 60 of the head member 16 is shown. Sleeve 18 slides over the mount 26 to increase the length or width of mount 26 (FIG. 2c), or to alter the angle at which the head member 16 extends from the body member 14, if anteversion is desired (FIG. 8). As shown in FIG. 8, sleeve 18 has an inner surface 90 and an outer surface 92 defining a wall 96 therebetween. The wall 96 thickness can vary gradually to position the head member 16 at an acute angle relative to the longitudinal axis 6 of the body member 14.

Figure 6B:
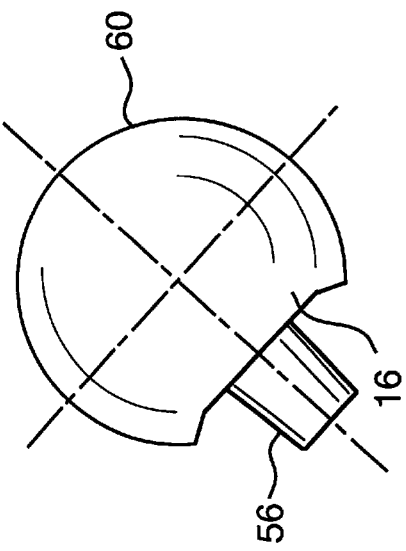
FIGS. 6a and b illustrate two alternative modular head members, an anteverted head member and an enlarged head member.
Figure 6A:
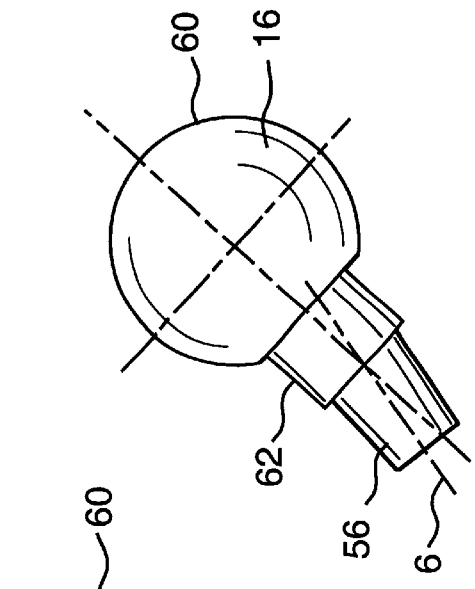
Figure 5:
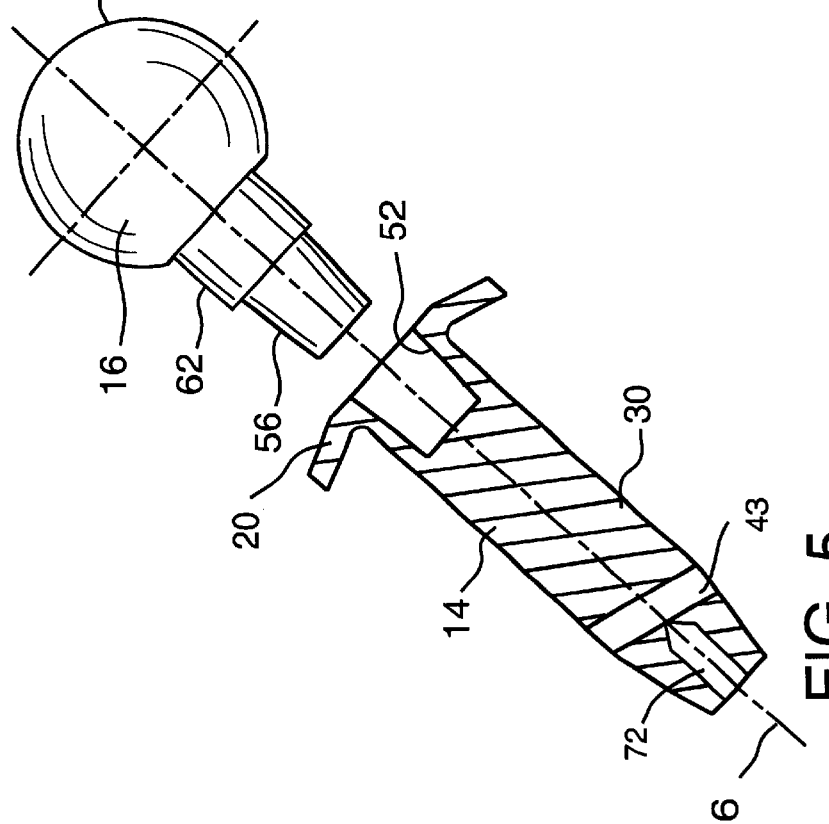
FIG. 5 is a view of an alternative embodiment of the body and head members of the implant of the present invention showing the mounting member as part of the head member.

The head and body members, 16 and 14 respectively, of the embodiment of the implant 10 of the present invention, shown in FIGS. 1 and 2, are in axial alignment with each other. However, several embodiments of implant 10 are configured for providing anteversion to permit the spherical portion 60 of head member 16 to mate with the patient's hip socket at an angle relative to the longitudinal axis of the shaft 30. Referring to FIGS. 3a and 3b, the mount 26 may extend at an angle from the central axis of the shaft 30. When the head member 16 is positioned on the mount 26, the head member 16 will be angled relative to the longitudinal axis of the shaft 30. Referring to FIG. 6a, the embodiment of head member 16 having a mount 56 may be configured such that the central axes of the spherical portion 60 and the annular portion 62 form an acute angle relative to the axis of the mount 56 and the body member 14 when the components are joined. In yet another embodiment, the anteversion may be achieved by angulation of recess 28 in head member 16.

Alternatively, body member 14, mount 26, and head member 16 may be formed as a unitary structure as shown in FIGS. 7a, 7b, and 7c having integrally attached portions joining the head and body members, 16 and 14 respectively. Embodiments with and without a collar 20, a porous coating 22 and anteversion (FIG. 7a) are provided.

Referring to FIGS. 9&10, the rod 44 may further comprise one or two stabilizing passages 46. Each stabilizing passage 46 is in a direction transverse to the longitudinal axis 45 of the rod 44 and may be located at any point along the longitudinal axis 45 of the rod 44, but is preferably located toward the distal end of the rod 44. The stabilizing passage 46 enables a surgeon to insert a fastener, preferably a bone screw 70, from one side of the femur 12 and through the passage 46 to the other side of the femur 12, and preferably from the lateral side of the femur 12 and through the passage 46 to the medial side of the femur 12. The passages 46 and the bone screws 70 further stabilize the implant 10 within the femur 12.

An alternative embodiment of the implant 10 is shown in FIG. 13. The rod 44 is a dual tapered wedge, the taper preferably being wider at the proximal end than at the distal end, as illustrated in FIG. 13a. The body member 14 in the alternative embodiment, as illustrated in FIGS. 13a and b, is similar to the body member 14 described above, except that the transverse passage 43 is shaped to accept and complementarily engage the rod 44. Preferably, and as shown in FIG. 13b, the transverse passage 43 is rectangular and has walls (shaded) such that the tapered wedge of the rod 44 can slidingly engage the body member 14. An advantage to the dual tapered wedge design is that it does not require a stabilizing passage 46 and fastener because, in use, the sharp surfaces of the rod 44 contact the cortical surfaces in the bone and eliminate the need for a fastener. Furthermore, the alternative embodiment of the rod 44 can include any one of the variations of body members 14 described above. Although the dual (diamond shaped) taper is preferred, a triangular shape or any other multiple sided taper that can engage the cortical surfaces in the femoral canal will suffice. By engaging the cortical surfaces, the need for passages 46 and bone screws 70 through the femur is eliminated. In addition, the shape inhibits rotation of the rod 44 within body member 14.

In addition, the implant 10 may further comprise a locking fastener, preferably a locking screw 71, and a locking passage 72. The locking passage 72 is located along the longitudinal axis 6 of the shaft 30 and is in at least a portion of the distal end 50 of the body member 14. The locking passage 72 enables a surgeon to insert a locking screw 71 from the lateral side of femur 12, below the greater trochanter 2, into the passage 72 and into the body member 14, thus securing the implant 10 within the femur 12.

Figure 12:
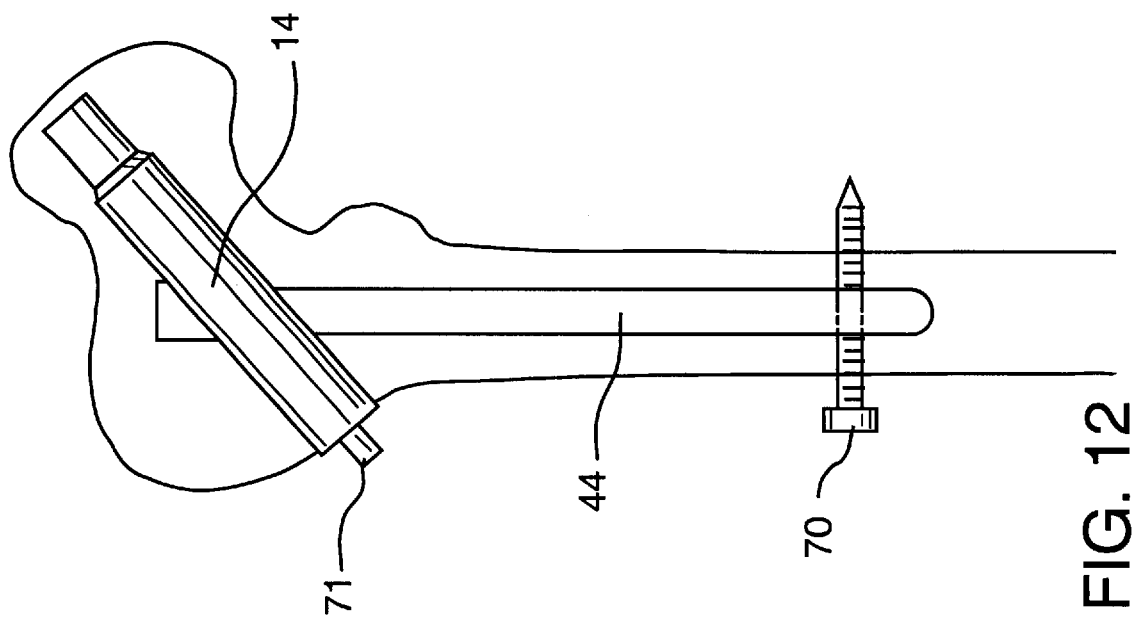
FIG. 12 illustrates an embodiment of the implant overlayed on a femur.
Figure 11:
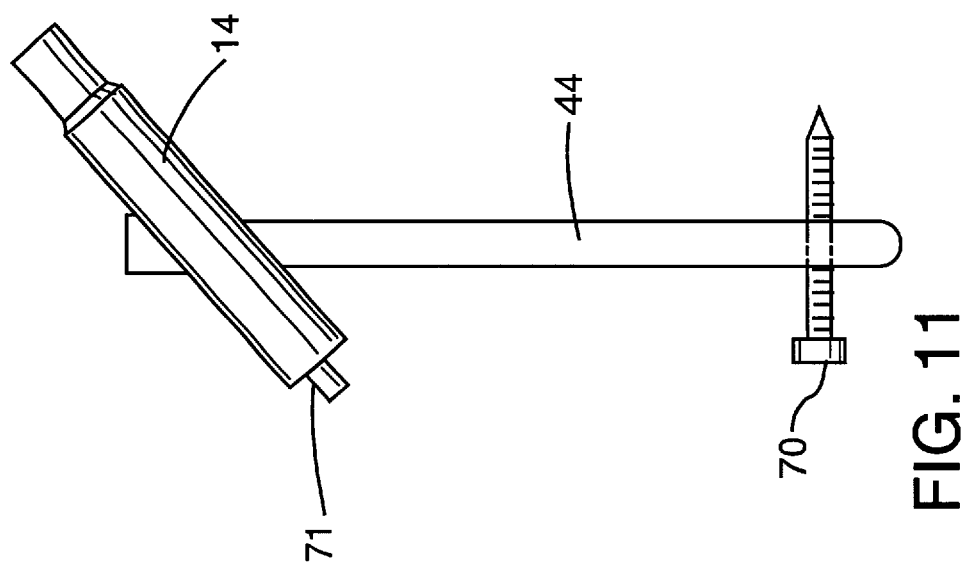
FIG. 11 illustrates an embodiment of the implant.

Referring to FIG. 11, an embodiment of the implant 10 (without head member 16) is shown as it appears when not implanted in a femur 12. FIG. 12 illustrates an embodiment of the implant 10 (without head member 16) overlayed on a femur 12 to illustrate how the implant 10 would fit within a femur 12.

Any bio-compatible material may be employed for the materials of the present invention. Suitable materials include, but are not limited to, stainless steel, titanium and cobalt. Any bio-compatible textures or coatings that engage the bone or that promote bone ingrowth may be utilized with the present invention.

Figure 14:
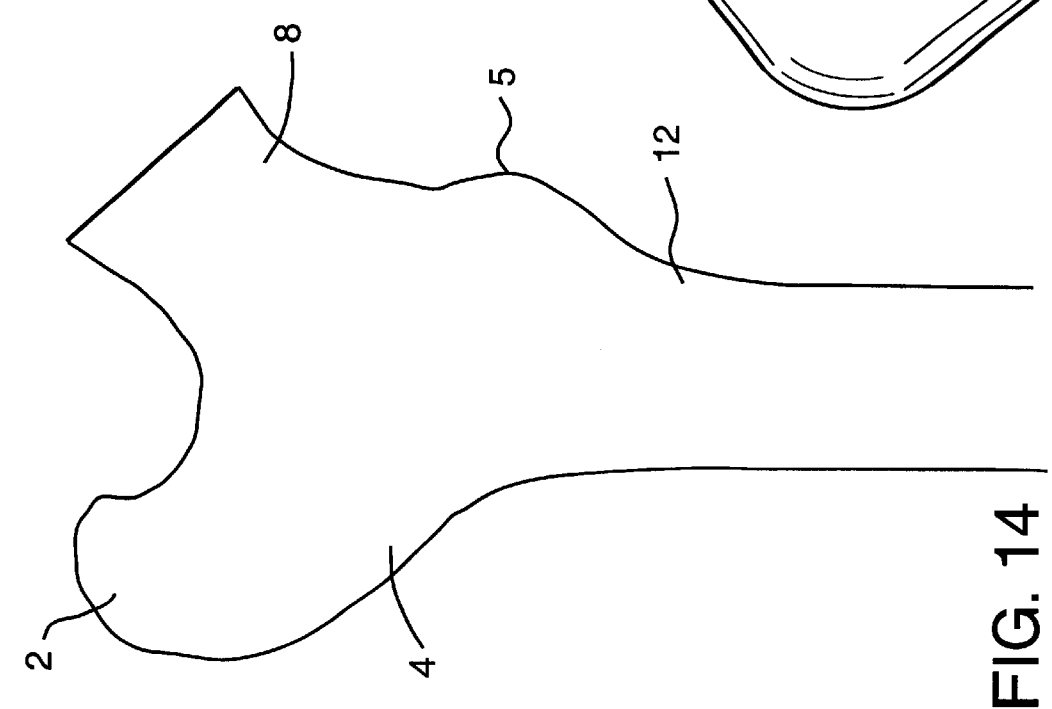

FIGS. 14–20 illustrate one method of implanting the implant 10 in a femur 12. An incision can be made along the lateral side at the hip of the patient. The muscle surrounding the hip is then separated and the hip is dislocated. The natural femoral head is then removed by, for example, sawing the femur 12 such that the femur 12 is left intact up to and including most or all of the femoral neck 8, as illustrated in FIG. 14.

Figure 15:
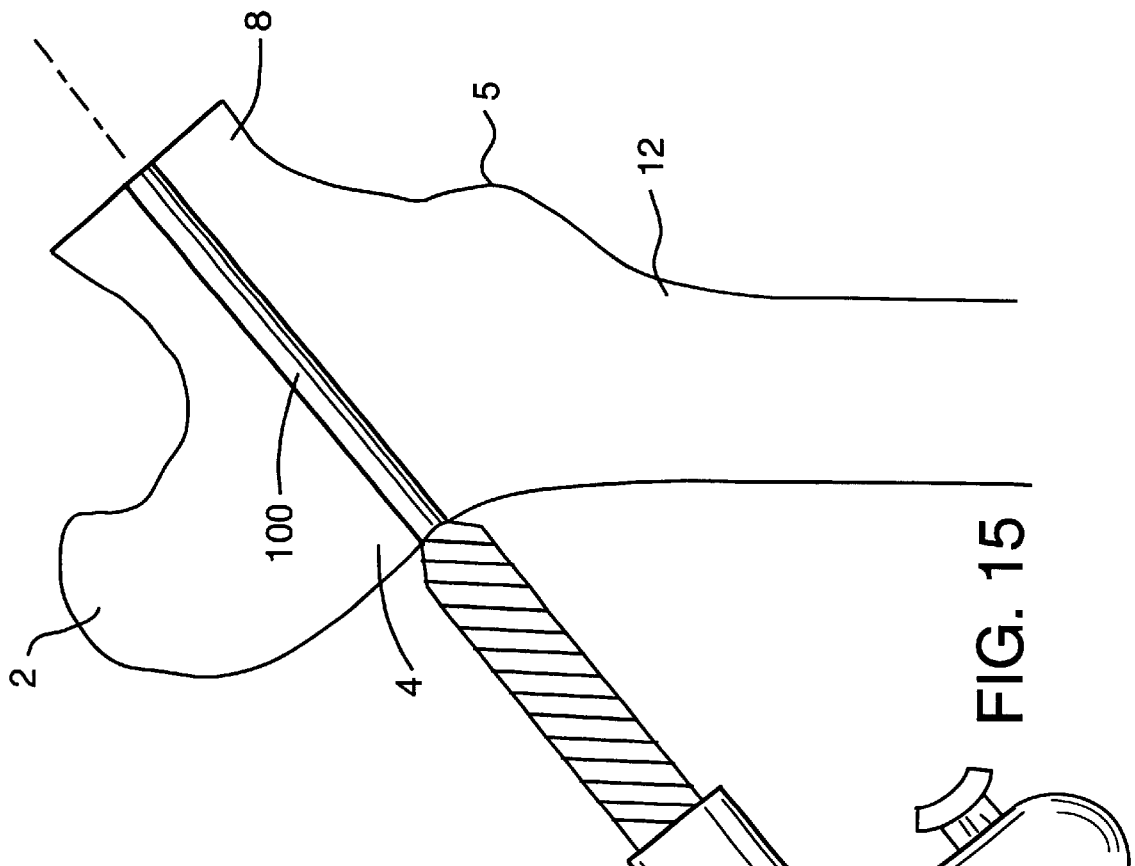
FIGS. 14–18 illustrate schematically the procedure for removal of the femoral head and the implantation of the proximal femoral implant of the present invention.

As shown in FIG. 15, the next step of the method is to insert a pin, preferably a Steinmann Pin, along the longitudinal axis of the neck 8 of the femur 12. The pin is inserted from the lateral side of the femur 12 at a point below the greater trochanter 2 towards the head of the femur (which has been removed). A canal 100 is then reamed along the longitudinal axis of the neck 8 of the femur 12 to receive the body member 14 of the implant 10.

Figure 16:
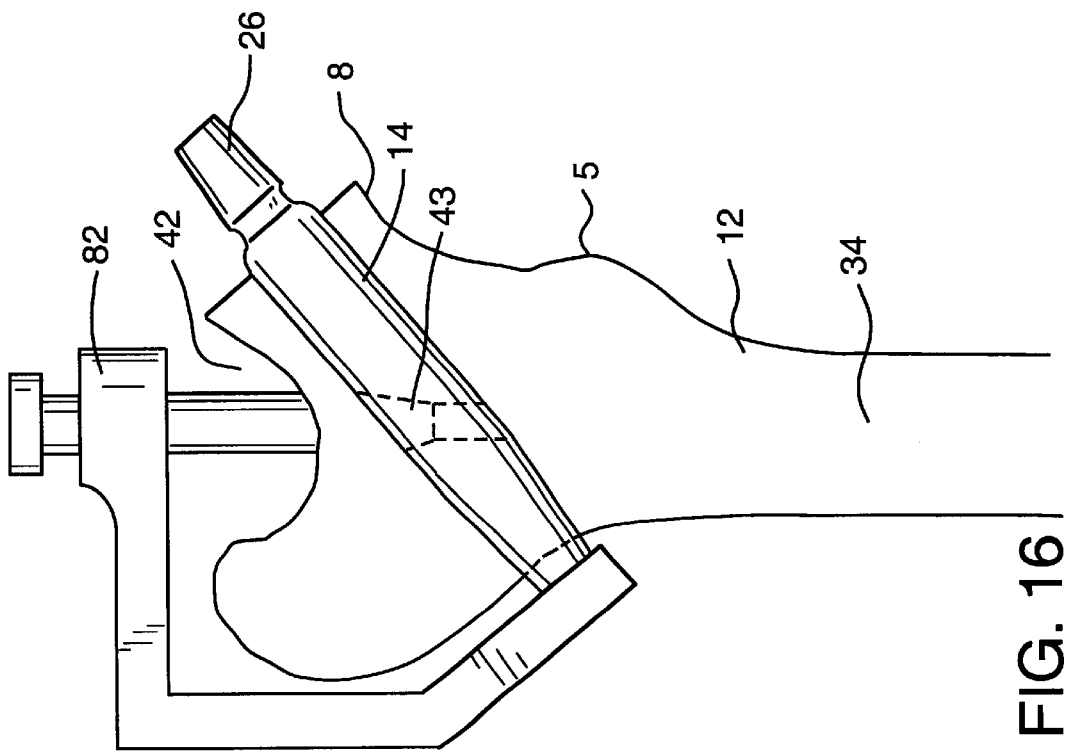

Referring to FIG. 16, the body member 14 is then assembled, if necessary, and driven into the canal 100 such that the proximal end of the body member 14 extends through the femoral neck 8 and the distal end 50 of the body member 14 is in the extramedullary area 4 of the femur 12. Next, a canal alignment fixture 82 (FIG. 19) is fitted to the body member 14 and aligned for use as a drill guide. The canal alignment fixture 82 provides the proper neck shaft reference location for drilling into the medullary canal 34. A drill bit may then be inserted through the drill sleeve of the canal alignment fixture 82 and used to drill through the proximal end 42 of the femur 12, through the pre-existing transverse passage 43 in the shaft 30 of the body member 14 and into the medullary canal 34 of the femur 12. The drill sleeve and bit should be sized so that the rod 44 may fit through the transverse passage 43 of the body member 14. Preferably, the drilling sleeve is sized to accept a 9 mm reamer.

Figure 17:
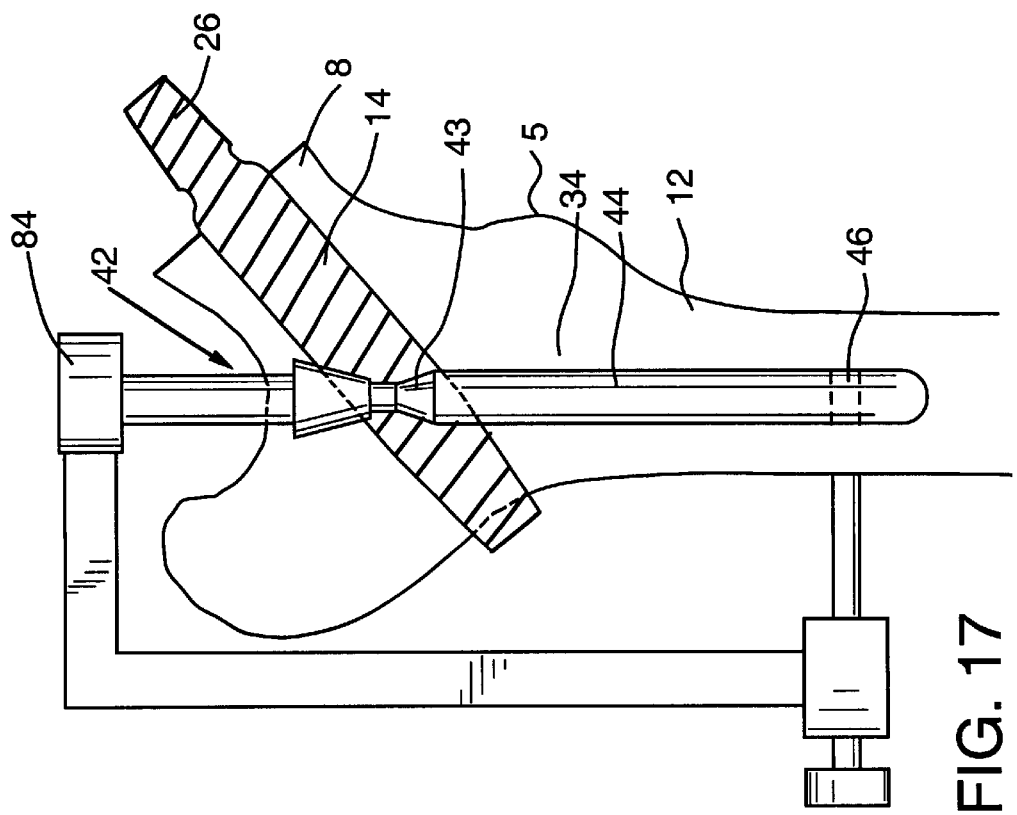

The next step in the method is to assemble the rod 44, if necessary, and drive the rod 44 from the proximal end 42 of the femur 12, through the transverse passage 43 of the shaft 30 of body member 14 and into the medullary canal 34 of the femur 12, as shown in FIG. 17. Next, a distal drilling alignment fixture 84 is fitted to the proximal end of the rod 44 and aligned for use as a drill guide. The distal drilling alignment fixture 84 provides alignment between the shaft 30 of the body member 14 and the distal end of the rod 44. A drill bit may then be inserted through the drill sleeve of the distal drilling alignment fixture 84 and used to drill through the femur 12, through the pre-existing stabilizing passage 46 in the distal end of the rod 44 and into the medial side of the femur 12. The drill bit should be sized so that a fastener, preferably a bone screw 70, may fit through the stabilizing passage 46 in the rod 44.

Figure 18:
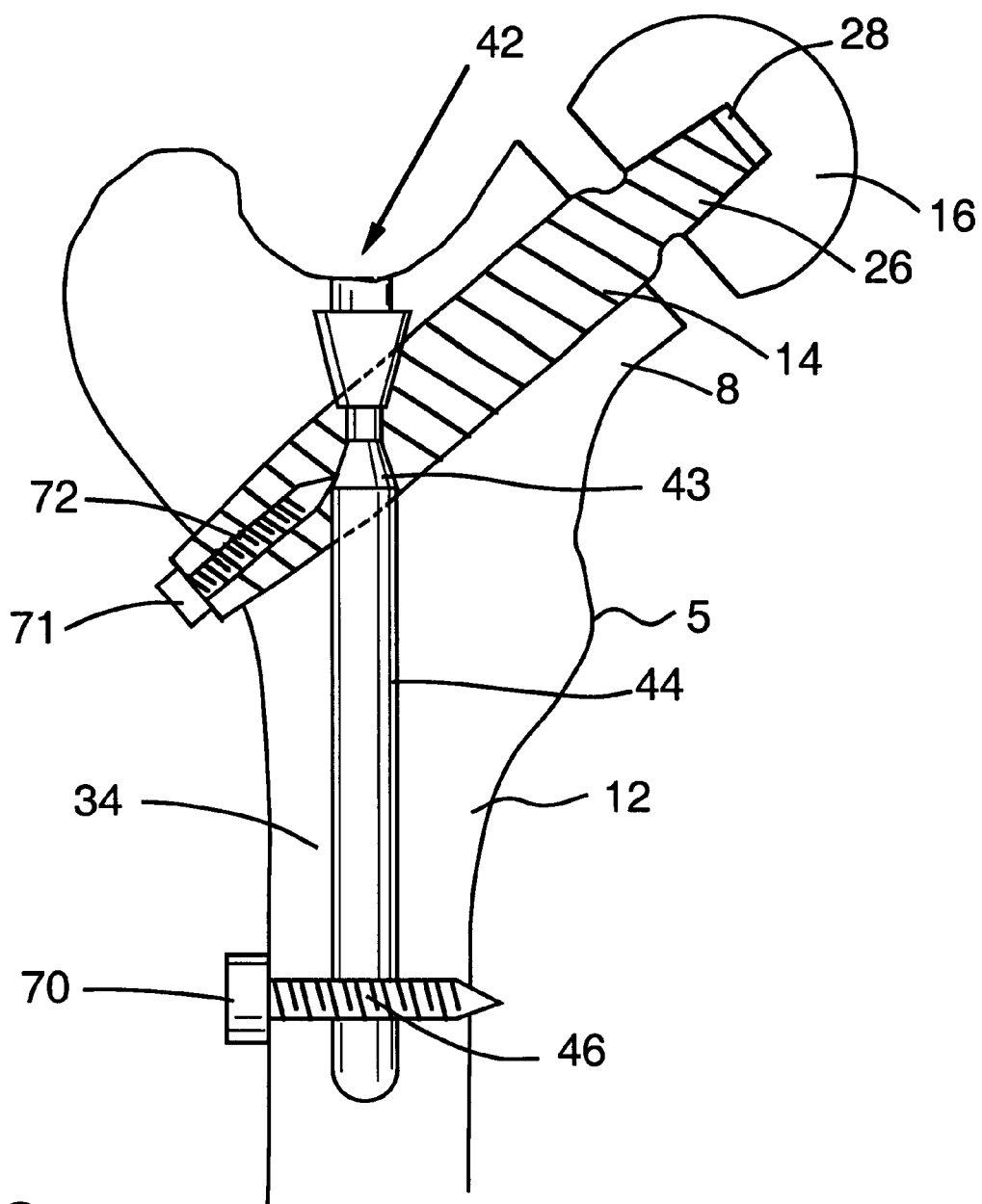

Another step of the method, as shown in FIG. 18, is to insert a fastener, preferably a bone screw 70, through the stabilizing passage 46. The bone screw 70 secures the rod 44 and the remainder of the implant 10 into the femur 12. In addition, a locking fastener, preferably a locking screw 71, may also be inserted into a locking passage 72 in the body member 14.

The above described method is modified when using the alternative embodiment of the implant 10 illustrated in FIG. 13. As stated previously, the alternative embodiment of the implant 10 has a rod 44 that has a cross-sectional configuration of a tapered wedge and the body member 14 has a transverse passage 43 that can complementarily engage the tapered wedge. The use of the canal alignment fixture 82 is the same as above except special care should be taken to ensure that the drill bit does not adulterate the differently shaped transverse passage 43. Then, a broach is used to insert the rod 44. In addition, there is no need to use a distal drilling alignment fixture 84 because the dual tapered wedge embodiment does not require the use of a stabilizing passage 46 and fastener.

After implanting either embodiment of the implant 10, the head member 16 is then impacted onto the mount 26 of body member 14. If an extension in length or width or a change in angle is desired, a suitable embodiment of the optional sleeve 18 may be placed over the mount 26 prior to placement of the head member 16 onto the body member 14.

Figure 19:
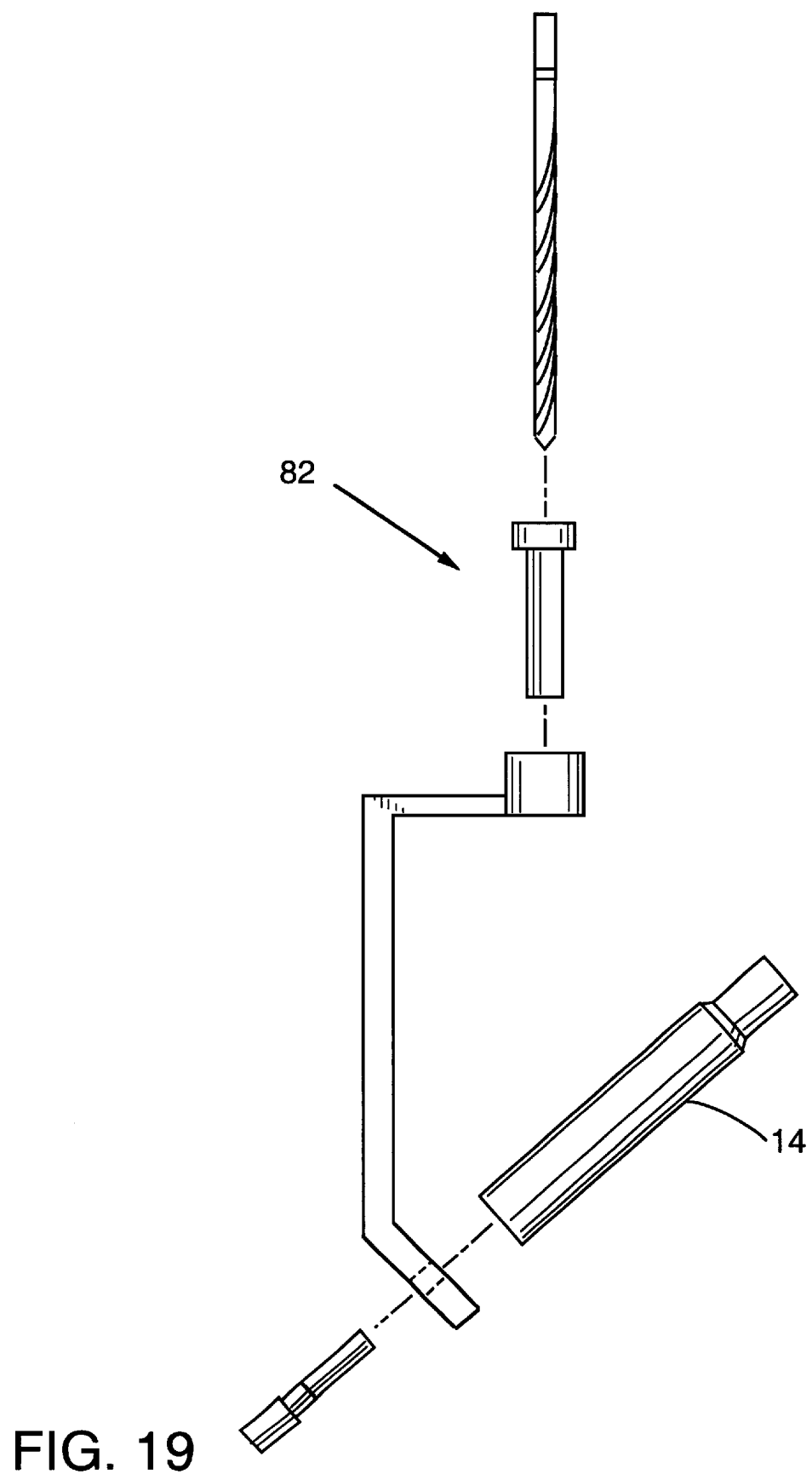
FIG. 19 is an exploded view of a canal alignment fixture and drill bit as it would be fitted to the body member to form a transverse passage.

FIG. 19 is an exploded view of a canal alignment fixture 82 and drill bit as it would be fitted to the body member 14. As stated previously, the canal alignment fixture 82 may be used to form a transverse passage 43.

Figure 20:
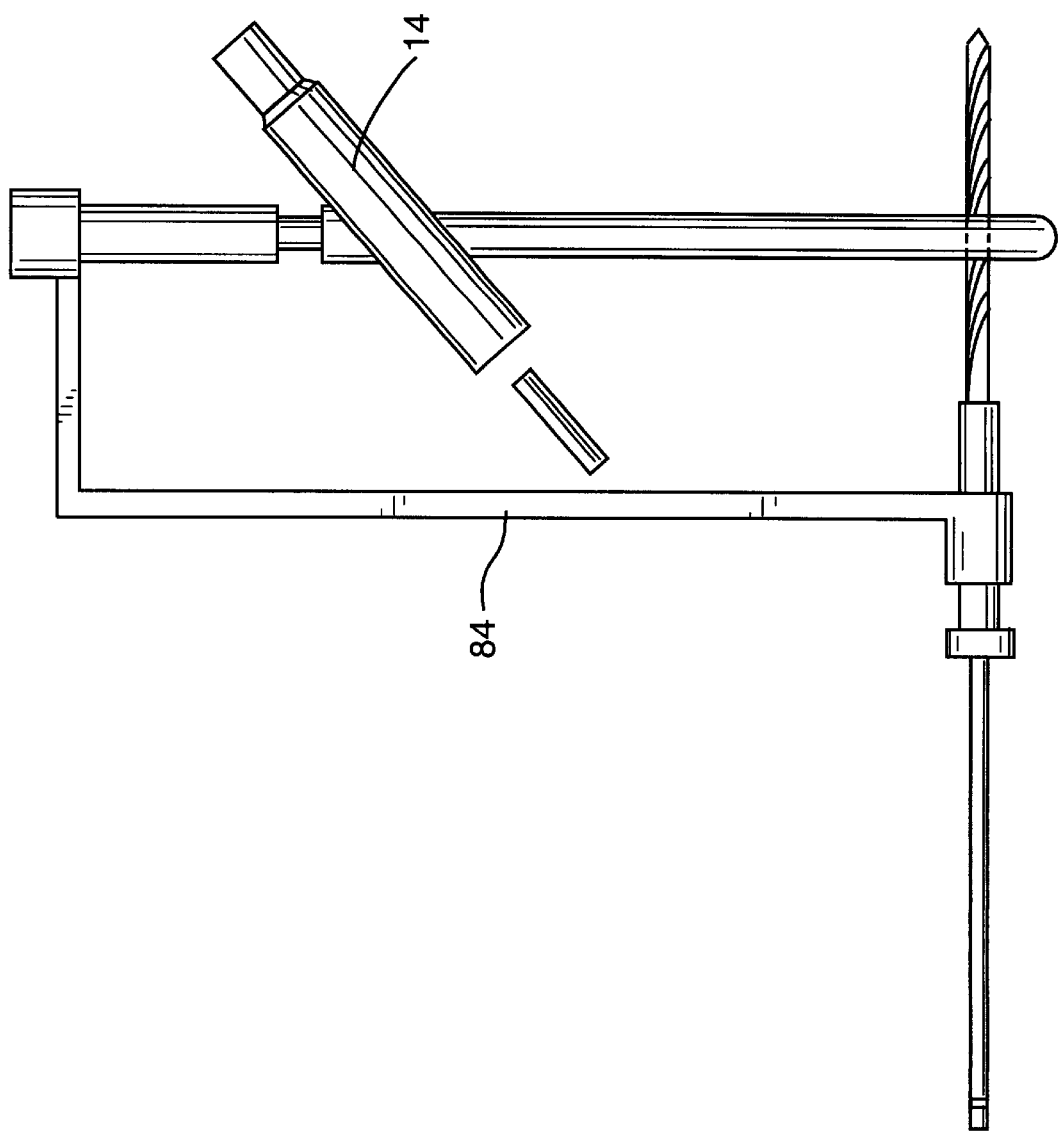
FIG. 20 illustrates a distal drilling alignment fixture and drill bit as it would be fitted to the rod to form a stabilizing passage.

FIG. 20 illustrates a distal drilling alignment fixture 84 and drill bit as it would be fitted to the rod 44. As stated previously, the distal drilling alignment fixture 84 may be used to form a stabilizing passage 46.

Figure 21:
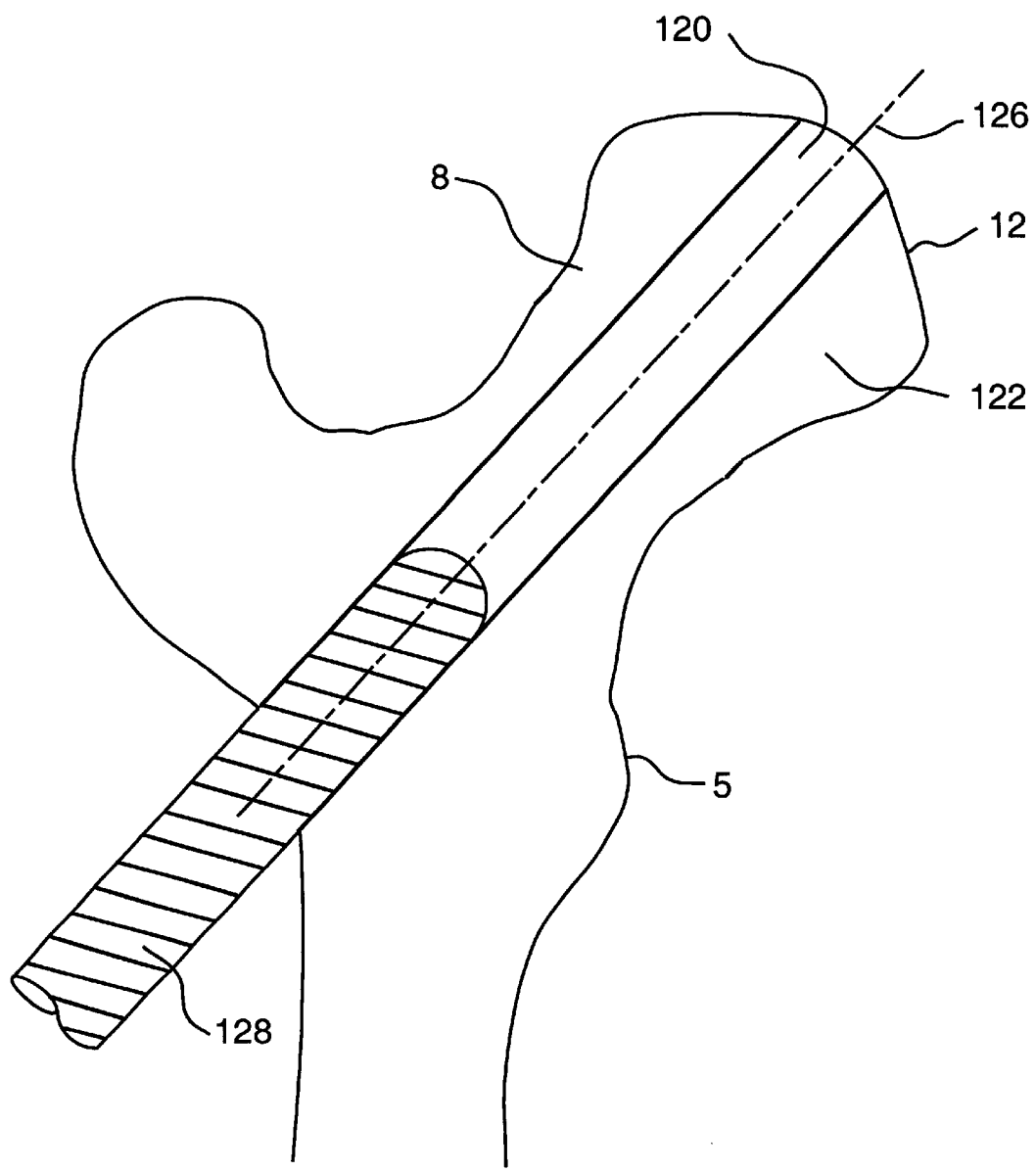
FIGS. 21 and 22 illustrate an alternative method for implanting the body member of the proximal femoral implant of the present invention.
Figure 22:
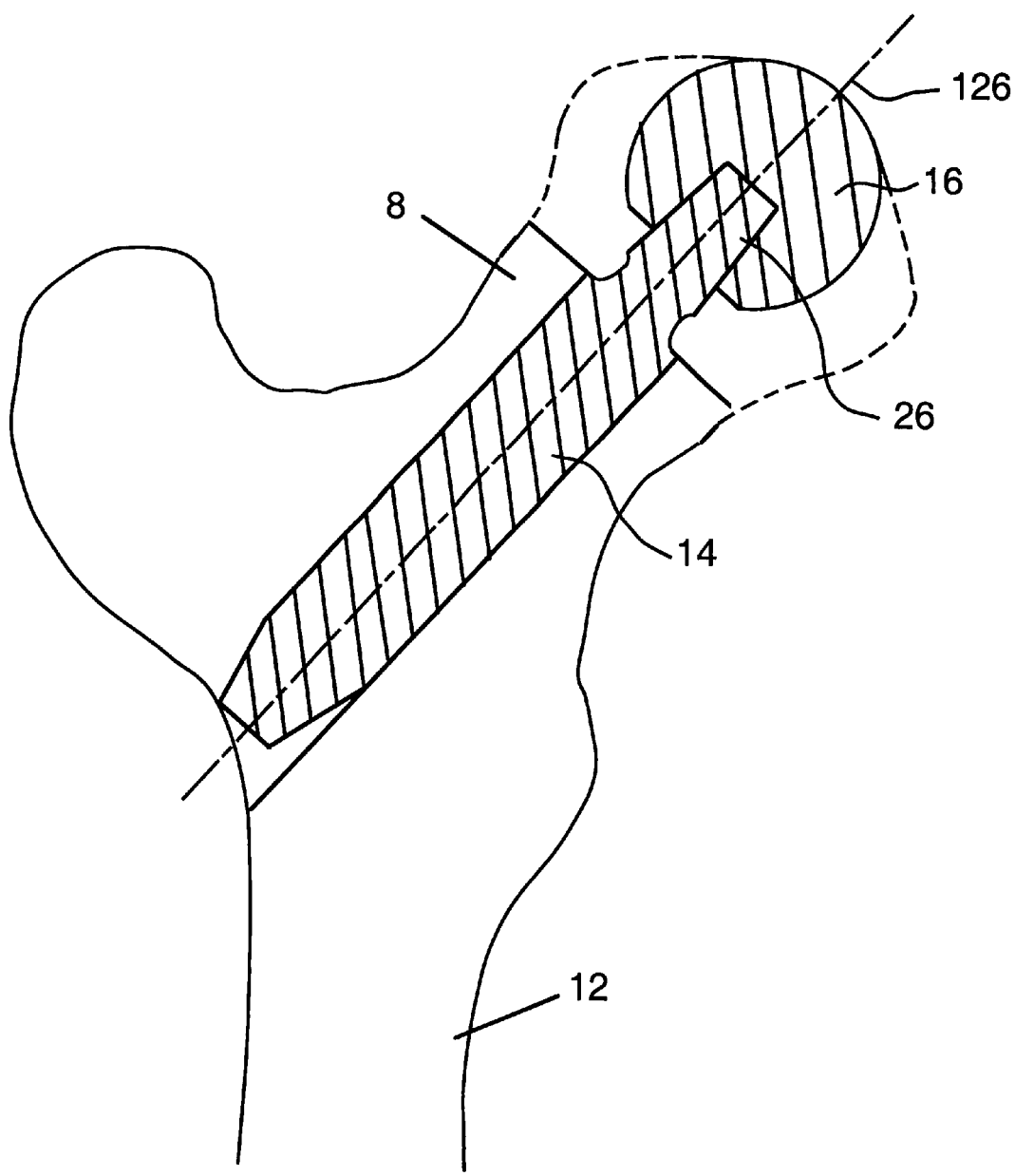

FIGS. 21 and 22 illustrate an alternative method of implanting the body member 14 of the implant 10 of the present invention into the patient, which is less invasive than conventional methods. FIG. 21 is a cross-sectional view of the femur 12 with a passage 120 that is substantially co-axially aligned with the axis 126 of the femoral neck 8. FIG. 22 illustrates the body member 14 and head member 16 of the proximal femoral implant 10 of the present invention, shown in FIG. 2b, implanted within the femur 12.

First, an incision at the lateral side of the hip is made of a size such that a reamer or burr 128 can be inserted into the patient and engage the femur 12 at the lateral side thereof and along the longitudinal axis 126 of the femoral neck 8. The size of this incision is substantially smaller than the incision made when the hip must be dislocated to sever the femoral head, as is the case with conventional methods of implantation. The reamer or burr 128 then reams a substantially cylindrical passage 120 through the femur 12 along the axis 126.

Alternatively, a series of reamers or burrs 128 can be used to achieve the desired diameter of the passage 120. A first reamer reams a passage 120 along the axis 126 of the femoral neck 8, then a second reamer having a larger diameter than the first reamer enlarges the diameter of the passage 120. The number of reamers used is dependent on the patient and the desired size of the passage 120. By enlarging the diameter of the passage incrementally, less damage is done to the femur 12.

The femoral head 122 is then morselized using an instrument positioned within the passage such as a reamer or burr. The small pieces of the femoral head 122 are then suctioned from the patient's hip and the surface of the resected femoral neck is shaped as desired.

In the case where it is necessary to reshape the natural acetabular cup (not shown) to correspond with the shape of the head member 16, a reamer having a collapsible cutting portion can be inserted through the passage 120 with the reamer in its collapsed position and opened when the collapsible cutting portion extends through the passage 120 at the medial side of the femur 12. The rotating cutting portion of the reamer is then brought into engagement with the natural acetabular cup to shape the cup to correspond with the shape of the head member 16.

In the case where the acetabular cup needs to be replaced, a small incision at the medial side of the hip must be made to insert the acetabular cup implant. The acetabular cup implant can be attached to the patient by any conventional method.

Once the acetabular cup is prepared, the body member 14 of the implant 10, shown in FIG. 2b, is inserted into the passage 120 using an impactor (not shown) such that the body member 14 is press-fitted within the femur 12 and the mount 26 is positioned such that it extends above the femoral neck 8. A torque limiting wrench (not shown) may then be attached to the tapered mount 26 of the body member 14 and an amount of force, corresponding to the physiologic loading levels, may be applied to verify the stability of the body member 14. If an incision has not already been made to insert an acetabular cup implant, as noted above, a small incision must be made at the medial side of the hip and the head member 16 must be joined with the body member 14 at the mount 26.

Because the hip does not have to be dislocated and large incisions through muscle and tissue do not have to be made to implant the implant 10 of the present invention, the method of implantation of the present invention is less invasive than conventional methods.

The implant 10 of the present invention thus solves many of the problems encountered by prior femoral head replacement prostheses. Those of ordinary skill in the art will appreciate that various changes in the details, methods, materials and arrangement of parts which have been herein described and illustrated in order to explain the nature of the invention may be made by the skilled artisan within the principle and scope of the invention as expressed in the appended claims.

What is claimed is:

1. An implant for replacing the proximal portion of a femur having a substantially intact natural femoral neck, medial side, lateral side, greater trochanter and lesser trochanter, the implant comprising:

a body member having a longitudinal axis, a distal end and a proximal end and being configured for positioning, in use, in the natural femoral neck, wherein the body member has a transverse passage through at least a portion of the distal end in a direction transverse to the longitudinal axis of the body member;

a head member having a distal end and a proximal spherical portion configured for positioning in a natural or prosthetic hip socket;

a joining portion positioned between the distal end of the head member and the proximal end of the body member; and a rod having a longitudinal axis, a proximal end and a distal end and being configured for positioning, in use, through the transverse passage of the body member and for extension, in use, into the natural medullary canal of the femur in engagement with the cortical surface of the natural medullary canal.

2. The implant recited in claim 1 wherein the body member is configured for positioning, in use, in the natural femoral neck without passage of the distal end through the lateral side of the femur.

3. The implant recited in claim 1 further comprising a collar positioned at the proximal end of the body member and configured for abutting contact, in use, with a proximal surface of the resected femoral neck.

4. The implant recited in claim 1 wherein the body member and the head member are integrally attached at the joining portion.

5. The implant recited in claim 4 wherein the joining portion extends outwardly from the body member at an acute angle relative to the longitudinal axis of the body member.

6. The implant recited in claim 4 wherein the joining portion extends outwardly from the body member in substantial coaxial alignment relative to the longitudinal axis of the body member.

7. The implant recited in claim 4 further comprising a collar positioned at the proximal end of the body member and configured for abutting contact, in use, with a proximal surface of the resected femoral neck.

8. The implant recited in claim 1 wherein the body member and the head member are separable modular components.

9. The implant recited in claim 8 wherein the joining portion comprises a first engagement portion and a second engagement portion, said engagement portions being configured for complementary engagement with each other.

10. The implant recited in claim 9 wherein the first engagement portion is a recess for receiving the second engagement portion and the second engagement portion comprises a protrusion configured for insertion into the recess.

11. The implant recited in claim 10 wherein the protrusion has an axis which, in use, is at an acute angle relative to the longitudinal axis of the body member.

12. The implant recited in claim 10 wherein the protrusion has an axis which, in use, is in substantial co-axial alignment to the longitudinal axis of the body member.

13. The implant recited in claim 10 wherein the protrusion extends from the distal end of the head member and the recess is within the proximal end of the body member.

14. The implant recited in claim 10 wherein the recess is within the distal end of the head member and the protrusion extends from the proximal end of the body member.

15. The implant recited in claim 10 further comprising a sleeve for altering the position of the spherical portion of the head member relative to the body member.

16. The implant recited in claim 15 wherein the sleeve is longer than the protrusion for extending the distance between the spherical portion and the body member.

17. The implant recited in claim 15 wherein the sleeve has an inner surface and an outer surface and is mountable, in use, such that the inner surface slides over the protrusion and the outer surface is received within the recess.

18. The implant recited in claim 17 wherein the sleeve defines a wall between the inner surface and the outer surface, the wall having non-uniform, gradual thickness changes such that, in use, the central axis of the sleeve is at an acute angle relative to the longitudinal axis of the body member.

19. The implant recited in claim 8 further comprising a collar positioned at the proximal end of the body member and configured for abutting contact, in use, with a proximal surface of the resected femoral neck.

20. The implant recited in claim 1 further comprising a first surface coating on at least a portion of the body member for promoting bone ingrowth into the coating following implantation.

21. The implant recited in claim 20 further comprising a second surface coating on at least a portion of the first surface coating.

22. The implant recited in claim 1 further comprising a first surface coating on at least a portion of the rod for promoting bone ingrowth into the coating following implantation.

23. The implant recited in claim 22 further comprising a second surface coating on at least a portion of the first surface coating.

24. The implant recited in claim 1 wherein the body member is configured in cross-section to inhibit rotational motion of the body member following implantation.

25. The implant recited in claim 24 wherein the body member is triangular in cross-section.

26. The implant recited in claim 24 wherein the body member is fluted in cross-section.

27. The implant recited in claim 24 wherein the body member is scalloped in cross-section.

28. The implant recited in claim 1 wherein the body member is circular in cross-section.

29. The implant recited in claim 1 wherein the distal end of the body member is closed.

30. The implant recited in claim 1 further comprising a locking passage through at least a portion of the body member in a direction substantially coaxial to the longitudinal axis of the body member.

31. The implant recited in claim 30 further comprising a locking screw for passage into the locking passage.

32. An implant for replacing the proximal portion of a femur having a substantially intact natural femoral neck, medial side, lateral side, greater trochanter and lesser trochanter, the implant comprising:
  a body member having a longitudinal axis, a distal end and a proximal end and being configured for positioning, in use, in the natural femoral neck,
    wherein the body member has a transverse passage through at least a portion of the distal end in a direction transverse to the longitudinal axis of the body member;
  a head member having a distal end and a proximal spherical portion configured for positioning in a natural or prosthetic hip socket;
  a joining portion positioned between the distal end of the head member and the proximal end of the body member; and
  a rod having a longitudinal axis, a proximal end and a distal end and being configured for positioning, in use, through the transverse passage of the body member,
  the rod having a stabilizing passage through at least a portion of the rod in a direction transverse to the longitudinal axis of the rod.

33. The implant recited in claim 32 wherein the rod, in use, extends in substantially coaxial alignment relative to the longitudinal axis of the femur.

34. An implant for replacing the proximal portion of a femur having a substantially intact natural femoral neck, medial side, lateral side, greater trochanter and lesser trochanter, the implant comprising:
  a body member having a longitudinal axis, a distal end and a proximal end and being configured for positioning, in use, in the natural femoral neck,
    wherein the body member has a transverse passage through at least a portion of the distal end in a direction transverse to the longitudinal axis of the body member;

a head member having a distal end and a proximal spherical portion configured for positioning in a natural or prosthetic hip socket;

a joining portion positioned between the distal end of the head member and the proximal end of the body member; and a rod having a longitudinal axis, a proximal end and a distal end and being configured for positioning, in use, through the transverse passage of the body member, wherein the rod, in use, extends in substantially coaxial alignment relative to the longitudinal axis of the femur and the rod and the body member are slidably and lockingly engaged.

35. The implant recited in claim 34 wherein the locking engagement is a taper lock.

36. The implant recited in claim 34 further comprising a stabilizing passage through at least a portion of the rod in a direction transverse to the longitudinal axis of the rod.

37. The implant recited in claim 36 further comprising a bone screw for passage through the stabilizing passage.

38. The implant of claim 34 wherein the rod is a dual wedge in cross-section, wherein the dual wedge gradually tapers from the proximal end to the distal end, and wherein the transverse passage is configured to complement said dual wedge.

39. The implant recited in claim 38 further comprising a locking passage through at least a portion of the body member in a direction substantially coaxial to the longitudinal axis of the body member.

40. The implant recited in claim 39 further comprising a locking screw for passage into the locking passage.

41. An implant for replacing the proximal portion of a femur having a substantially intact natural femoral neck, medial side, lateral side, greater trochanter and lesser trochanter, the implant comprising:

a plurality of modular components of varying sizes within anatomical ranges for accommodating varying patient body dimensions, the components comprising:

a body member having a longitudinal axis, a distal end having a transverse passage in a direction transverse to the longitudinal axis of the body member and a locking passage in a direction substantially coaxial to the longitudinal axis of the body member, a proximal end having an engagement surface thereon, the body member being coated on at least a portion thereof with at least one layer of a material for promoting bone ingrowth and being configured for positioning, in use, in the natural femoral neck;

a head member having a distal end and a proximal spherical portion configured for positioning in a natural or prosthetic hip socket, the distal end of the head member having an engagement surface configured for complementary engagement with the engagement surface of the proximal end of the body member for joining the distal end of the head member to the proximal end of the body member;

a member for optionally altering the position of the spherical potion of the head member relative to the body member; and a rod having a proximal end and a distal end, wherein the rod extends through the transverse passage of the body member and is in substantially coaxial alignment relative to the longitudinal axis of the femur.

42. The implant recited in claim 41 wherein the engagement surface of the distal end of the head member is a recess and the engagement surface of the proximal end of the body member is a protrusion configured for insertion into the recess.

43. The implant recited in claim 42 wherein the protrusion has an axis which, when in engagement with the recess, is at an acute angle relative to the longitudinal axis of the body member.

44. The implant recited in claim 42 wherein the protrusion has an axis which, when in engagement with the recess, is in substantial co-axial alignment to the longitudinal axis of the body member.

45. The implant recited in claim 42 wherein the member for optionally altering the position of the spherical portion of the head member relative to the body member is a sleeve having an inner surface and an outer surface and being mountable, in use, such that the inner surface slides over the protrusion and the outer surface is received within the recess.

46. The implant recited in claim 45 wherein the sleeve is longer than the protrusion for extending the distance between the spherical member and the body member.

47. The implant recited in claim 46 wherein the sleeve defines a wall between the inner surface and the outer surface, the wall having non-uniform, gradual thickness changes such that, in use, the central axis of the sleeve is at an acute angle relative to the longitudinal axis of the body member.

48. The implant recited in claim 41 wherein the engagement surface of the distal end of the head member is a protrusion and the engagement surface of the proximal end of the body member is a recess configured for receiving the protrusion.

49. The implant recited in claim 48 wherein the protrusion has an axis which, when in engagement with the recess, is at an acute angle relative to the longitudinal axis of the body member.

50. The implant recited in claim 48 wherein the protrusion has an axis which, when in engagement with the recess, is in substantial co-axial alignment to the longitudinal axis of the body member.

51. The implant recited in claim 44 wherein the distal end of the rod further comprises a stabilizing passage that is in transverse alignment to the longitudinal axis of the femur.

52. The implant recited in claim 41 wherein the rod is a dual wedge in cross-section, wherein the dual wedge gradually tapers from the proximal end to the distal end, and wherein the transverse passage is configured to complement said dual wedge.

* * * * *

UNITED STATES PATENT AND TRADEMARK OFFICE
CERTIFICATE OF CORRECTION

PATENT NO.    : 6,616,697 B2
DATED         : September 9, 2003
INVENTOR(S)   : Nicholas G. Sotereanos It is certified that error appears in the above-identified patent and that said Letters Patent is hereby corrected as shown below:

<u>Title page,</u>
Item [*] Notice, should read as follows:
-- [*] Notice: Subject to any disclaimer, the term of this
               patent is extended or adjusted under 35
               U.S.C. 154(b) by 49 days. --.

Signed and Sealed this

Tenth Day of February, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,616,697 B2
DATED : September 9, 2003
INVENTOR(S) : Nicholas G. Sotereanos It is certified that error appears in the above-identified patent and that said Letters Patent is hereby corrected as shown below:

Column 14,
Line 2, delete "potion" and substitute -- portion --.

Signed and Sealed this

Second Day of May, 2006

JON W. DUDAS
*Director of the United States Patent and Trademark Office*